(12) United States Patent
Nourbakhsh et al.

(10) Patent No.: US 9,857,301 B1
(45) Date of Patent: Jan. 2, 2018

(54) AIR QUALITY SENSOR

(71) Applicant: Carnegie Mellon University, Pittsburgh, PA (US)

(72) Inventors: Illah Nourbakhsh, Pittsburgh, PA (US); Joshua Schapiro, Pittsburgh, PA (US); Chris Bartley, Pittsburgh, PA (US); Michael Taylor, Pittsburgh, PA (US)

(73) Assignee: CARNEGIE MELLON UNIVERSITY, Pittsburgh, PA (US)

( * ) Notice: Subject to any disclaimer, the term of this patent is extended or adjusted under 35 U.S.C. 154(b) by 396 days.

(21) Appl. No.: 14/684,542

(22) Filed: Apr. 13, 2015

Related U.S. Application Data (60) Provisional application No. 61/995,574, filed on Apr. 14, 2014.

(51) Int. Cl.
*G01N 21/47* (2006.01)
*G01N 33/00* (2006.01)

(52) U.S. Cl.
CPC ....... *G01N 21/4738* (2013.01); *G01N 33/007* (2013.01); *G01N 33/0062* (2013.01)

(58) Field of Classification Search
CPC ........... G01N 21/4738; G01N 33/0062; G01N 33/007
See application file for complete search history.

(56) References Cited

U.S. PATENT DOCUMENTS

| | | |
|---|---|---|
| 4,375,667 A | 3/1983 | Buchan |
| 5,467,189 A | 11/1995 | Kreikebaum et al. |
| 6,502,469 B2 | 1/2003 | Lawless |
| 6,693,546 B2 | 2/2004 | Skardon |
| 7,111,496 B1 * | 9/2006 | Lilienfeld .............. G01N 21/51 356/338 |
| 7,389,158 B2 | 6/2008 | Desrochers et al. |
| 8,009,290 B2 | 8/2011 | Unger |
| 8,085,145 B2 | 12/2011 | Fu et al. |
| 8,147,302 B2 | 4/2012 | Desrochers et al. |
| 8,150,465 B2 | 4/2012 | Zhang et al. |
| 8,161,830 B2 | 4/2012 | Boudries et al. |
| 8,204,786 B2 | 6/2012 | LeBoeuf et al. |
| 8,441,635 B2 | 5/2013 | Schubert et al. |
| 8,813,583 B2 | 8/2014 | Kilps et al. |
| 2004/0202547 A1 * | 10/2004 | Taylor .................... C01B 13/10 417/48 |
| 2005/0227625 A1 * | 10/2005 | Diener ................... H04B 17/23 455/67.7 |
| 2005/0243307 A1 * | 11/2005 | Silcott ................ G01N 15/1459 356/73 |

(Continued)

*Primary Examiner* — Manuel L Barbee
(74) *Attorney, Agent, or Firm* — K&L Gates LLP (57) ABSTRACT

Air quality sensor comprises an optical particle sensor and a programmable processor circuit. The optical particle sensor detects particles having a size of 10 microns or less in diameter in ambient air of the optical particle sensor. The programmable processor circuit continuously computes updated air quality measures for the ambient air using an estimation algorithm based on pulses in an output signal from the particle sensor over time, such as a cumulative particle density value and/or a cumulative particle weight value. The optical particle sensor may comprise a LED and accordingly detect particles based on reflection of light energy from the LED by particles in a chamber of the sensor.

25 Claims, 5 Drawing Sheets

(56) References Cited

U.S. PATENT DOCUMENTS

2010/0315638 A1\* 12/2010 Goohs .................. G01N 21/274
                     356/337
2013/0174646 A1\* 7/2013 Martin .................... G01N 33/00
                     73/31.02

\* cited by examiner

Fig. 1

```
<begin loop>
print current estimated particle density value
s = rolling sum of the last 5 1-second raw detector values
g = 4 x s
x = acquire current reading
d = g - x if d < -5000 then z = z - 250 else if d < -2500 then z = z - 130
else if d < -1200 then z = z - 60
else if d < -500 then z = z - 25
else if d < -5 then z = z - 5
else if d > 5000 then z = z + 500
else if d > 2500 then z = z + 250
else if d > 1200 then z = z + 130
else if d > 500 then z = z + 60
else if d > 5 then z = z+5 print z
<end loop>
```

AIR QUALITY SENSOR

PRIORITY CLAIM

The present application claims priority to U.S. provisional patent application Ser. No. 61/995,574, filed Apr. 14, 2014, entitled "Air Quality Particle Counting Sensor and Display," which is incorporated herein by reference in its entirety.

BACKGROUND

Existing air quality detectors fall into several categories that the inventors believe are inappropriate for the true market of measuring and displaying indoor air quality information to home residents in actionable ways. One type of existing device is an alarm-style device, using ionization of 0.05 micron-sized particles in order to detect nanoparticles in the air that represent smoke. These devices, essentially smoke detectors, present very loud audible warnings in a binary manner and are otherwise completely silent and lacking in user feedback. The second set of existing devices uses Volatile Organic Compound oxygen fuel cell style sensor chips to measure VOC content in the home air. However, these existing VOC sensors lack long-term calibration stability and report on volatile fluents rather than the ultrafine and fine particles that directly damage breathing and cause asthma attacks. Finally, a third category of devices measure Carbon Monoxide and/or Carbon Dioxide. While these molecule concentrations represent staleness of air (e.g. houses with no doors or windows open), these devices also fail to measure fine particulate concentrations that can embed themselves in the lung's alveoli.

In addition to these existing devices, HEPA filters that are used to clean indoor air commonly use dust sensors. However, these sensors are used as-is, with no forced air, and with the stochastic sensor readings only used to regulate air filter fan speed. Little feedback is provided to users in order to enable an understanding of how actions in the home, for instance, can directly impact air quality at an hourly and daily level. In addition, existing devices fail to provide strong uploading capabilities that tie into sharing and review on web-based applications, mobile applications and sharing and community-based problem solving in social media applications.

SUMMARY

In one general aspect, the preset invention is directed to an air quality sensor that reliably measures the concentration of fine particulates, accessibly stores air quality values over time, and displays air quality readings interactively. The benefits of this invention include the ability to accurately measure particulate concentration at low cost and the provisioning of actionable air quality data to home occupants.

These and other benefits of the present invention will be apparent from the description that follows.

FIGURES

Various embodiments of the present invention are described herein by way of example in connection with the following figures, wherein.

DESCRIPTION

Figure 1:
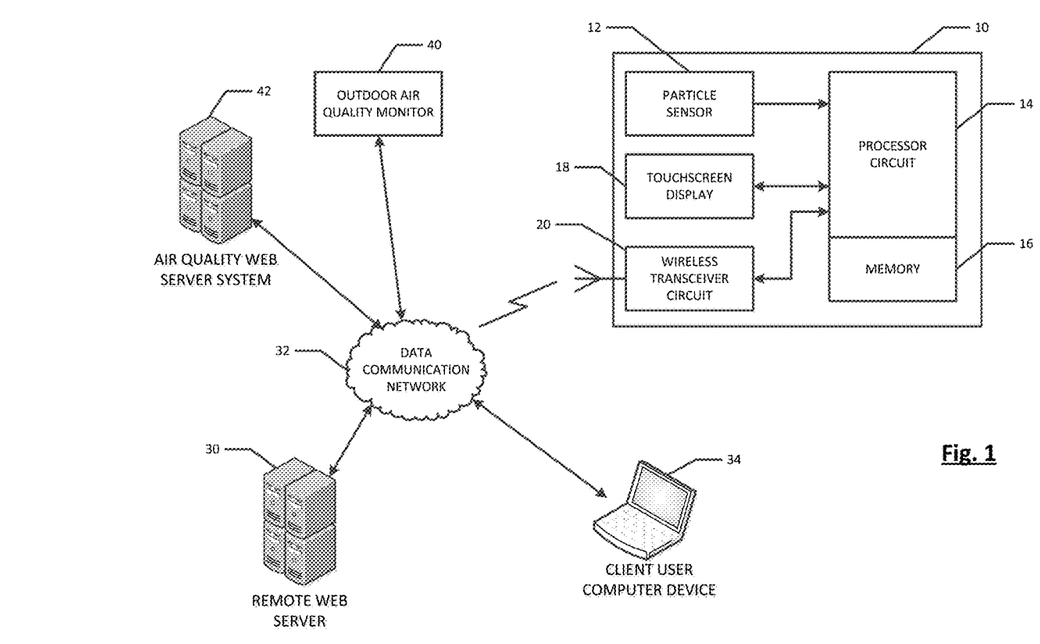
FIG. 1 is a block diagram of an air particle sensor according to various embodiments of the present invention.

FIG. 1 is a block diagram of an air quality sensor 10 according to various embodiments of the present invention. The illustrated air quality sensor 10 comprises an optical particle sensor 12, a programmable processor circuit (e.g., a microprocessor 14) with associated memory 16 (e.g., on-board memory), a touch-screen display 18, and a wireless transceiver circuit 20 (e.g., a Wi-Fi module, chip or chipset). The particle sensor 12 subjects incoming ambient air around the sensor 10 to infrared LED illumination and measures reflections of infrared light by detecting short-term, perpendicular reflections using a photodetector chip in order to detect and count particles in the air around the sensor. The optical particle sensor 12 can be designed to detect and count particles that are 10 microns or less in diameters, and preferably 0.3 to 10 microns. Fine airborne particles smaller than 2.5 microns, often denoted as $PM_{2.5}$, can pose serious health risks. Thus, the particle sensor 12 preferably detects $PM_{2.5}$ particles. The sensor 10 is preferably for indoor use, such as in a user's home. That way, with the sensor 10 the user can continuously monitor the air quality in their home.

The particle sensor 12 may be, for example, a DSM501A dust sensor. The sensor can include a fan forcing inflow of the sampling air, and measures the dispersion of reflected lights (from a LED) by particles. This measurement is converted to a pulse width modulated (PWM) output signal. In particular, the particle sensor 12 can include a digital output connected to the microprocessor 14, where the digital pin voltage is pulled low when particles are detected in the sensor's optical chamber, with the duty cycle being approximately proportional to the number of detected particles.

The microprocessor 14, by executing code stored in the memory 16, implements the air quality estimation algorithm, records raw particle sensor 12 output values, and uses these values to compute and store estimated particulate densities for the sensor's ambient air in memory 16. Additional resident firmware code in the memory 16 and executed by the processor 14 serves to control the pixels of the touch-screen display 18, which preferably is a color TFT touch-screen, in order to render interactive screens, detect screen touch events, and govern transition between separate interactive screen modes, including real-time mode (see FIG. 3) and historical review modes (see FIGS. 4 and 5). A color touch screen is preferable because different screen colors can be used to indicate different air quality conditions. These sample screens are described in more detail below.

While the duration of the low pulses from the particle sensor 12 (indicating detected particles) rarely exceeds 100 ms, the duration between pulses can last from under one second to more than one minute. Because single-cycle readings are typically too noisy to be used directly, in various embodiments the processor's algorithm samples the sensor output, such as 10,000 times per second. The number of low samples each second can be used by the processor's estimation algorithm to determine the particle count. In one embodiment, an asymmetric filtering function can be used. In one embodiment, the processor 14 can use the following piecewise function to continuously update the cumulative particle count estimate $est_t$ at time t, where $raw_t$ is the raw sensor value at time t:

$$est_{t=1} = \begin{cases} \dfrac{A*raw_t - est_t}{B} + est_t, & \text{where } raw_t > 0 \\ (1-D)*est_t, & \text{where } raw_t = 0 \end{cases} \quad \text{Equation (1)}$$

Figure 2:
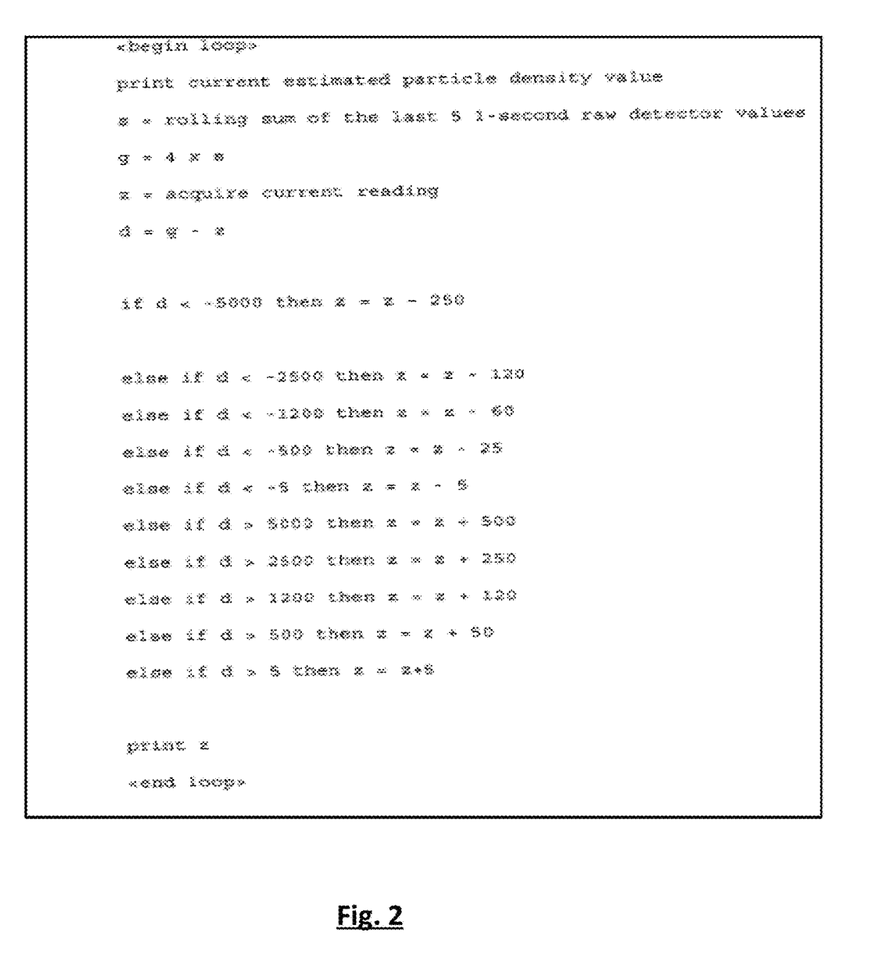
FIG. 2 is simplified code depicting the computational process of detecting dust sensor outputs, then computing an accurate estimate of fine particulate air pollution density based on the amplitude and timing of dust sensor outputs.

A, B, and D are constants that can be determined through a calibration process that is described below. As Equation 1 shows, if the raw value is non-zero, the current particle count estimate is incremented or decremented at a rate proportional to the difference between the estimate and the raw value scaled by a constant. If the raw value is zero, the estimate exponentially decays toward zero, preferably at a lower rate. The resulting behavior is that the particle count estimate quickly responds to non-zero raw values, but decays toward zero slowly due to the potential for long pauses between pulses. The processor 14 can also be programmed to convert the particle count to an estimated particle weight (e.g., micrograms per cubic meter). In one embodiment, the particle weight measurements can be obtained using a linear scale factor generated from fitting particle count data from one or more of the sensors 10 to another, co-located device used to measure particle concentrations, such as a tapered element oscillating microbalance (TEOM), FIG. 2 shows example pseudocode that can be executed by the processor 14 (and stored in the memory 16) in another embodiment in order to continuously compute updated, real time air quality measures for the ambient air in which the sensor 10 is located. The algorithm depicted in FIG. 2 corresponds to a combination of linear proportional transfer functions from raw particle count values detected by the particle sensor 12 that are accumulated to estimate the particle density (in this case, particles per liter). As shown in the example of FIG. 2, the quantity "s" is a rolling sum of the last several raw particle count values detected by the sensor 12. In the example of FIG. 2, the last 5 one-second raw particle count values are used. As shown in FIG. 2, the processor 14 computes two intermediate values that are used in computing the final air quality measure: "g" is the product of some constant (here, 4) and s (the rolling sum of last several raw particle count values), and "d" is g minus z where "z" is (initially) the current, real-time particle count detected by the sensor 12. The processor then adjusts z depending on the value for d according to the linear proportional transfer functions as shown in FIG. 2. For example, if d is less than −5000, then z=z−250; if d is less than −2500 (but more than −5000), then z=z−120; and so on as shown in FIG. 2. The final value for "z" corresponds to the instantaneous, cumulative air quality measure, and can be stored in memory 16 with a time stamp. The processor can also compute an estimated weight for the particles by using a conversion formula to convert it to micrograms per cubic meter, for example, as described above.

Figure 3:
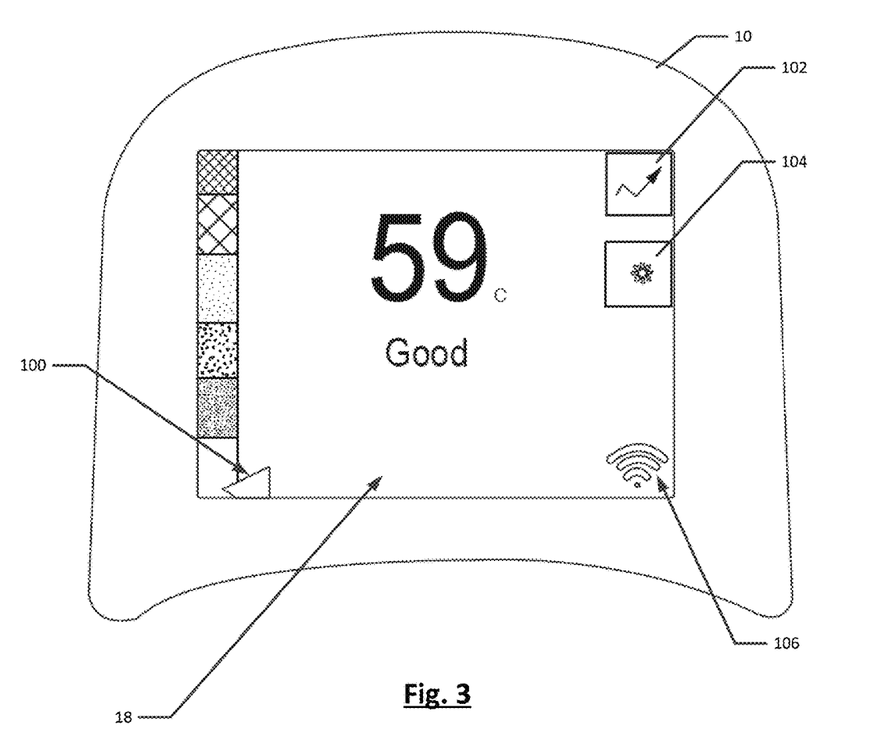
FIG. 3 is an interactive image of the real-time air pollution estimate shown on-screen in one instantiation of the invention.

FIG. 3 depicts an example default interactive screen mode, in which case the large-font number (in this example, "59") reports current air pollution levels as computed by the processor 14 as described above. The screen's displayed air quality value can be continuously updated as frequently as computed by the processor 14, such as every second or some other frequency. The screen background color preferably corresponds to a binned color palette that summarizes air quality from good to bad. That way, different background screen colors can easily indicate the air quality to the user. For example, the following color codes could be used:

| COLOR | COLOR CODE IN FIG. 3 | RATING | EST. PARTICLE COUNT (PPL) | EST. WEIGHT (mcg per cubic meter) |
|---|---|---|---|---|
| Blue | Clear | Good | 0 to 500 | 0 to 20 |
| Green | Dense Stippling | Moderate | 501 to 1000 | 21 to 40 |
| Light Green | Medium Stippling | Slightly Elevated | 1001 to 2000 | 41 to 80 |
| Yellow | Light Stippling | Elevated | 2001 to 4000 | 81 to 160 |
| Orange | Coarse Cross-hatch | High | 4001 to 8000 | 161 to 320 |
| Red | Fine Cross-hatch | Very High | 8001 to 1600 | 321 to 640 |

A full palette of the color codes can be shown along the left edge, with a triangular icon 100 pointing to the current level. Preferably the colors match; if the triangular icon 100 is pointing to blue (denoted as clear in FIG. 3, and indicating good air quality in this example), the background for the displayed air quality measure should be blue (denoted as clear in FIG. 3), and so on. This color-based indicator enables the occupant to glance at the air quality sensor and quickly comprehend the approximate, real-time air quality. Of course, in other embodiments, fewer or more levels can be used; the levels could correspond to different particle count or weight ranges; and different color schemes and be used. Furthermore the color palette can be configured by the user to operate across a colorblind-safe spectrum, providing more comprehensive accessibility.

In the example of FIG. 3, the air pollution estimate shown is reported in units of particles per liter, notated by the unit 'C.' A single touch of the touchscreen display 18 in the vicinity of the main, reported value at the center of the screen toggles between this reporting unit and micrograms per cubic meter, notated by the unit 'W' for weight. This toggle enables the user to compare their indoor air quality directly to both major forms of outdoor air quality reports fairly, enabling occupants to surmise the efficacy of their home at maintaining relatively clean air.

Figure 4:
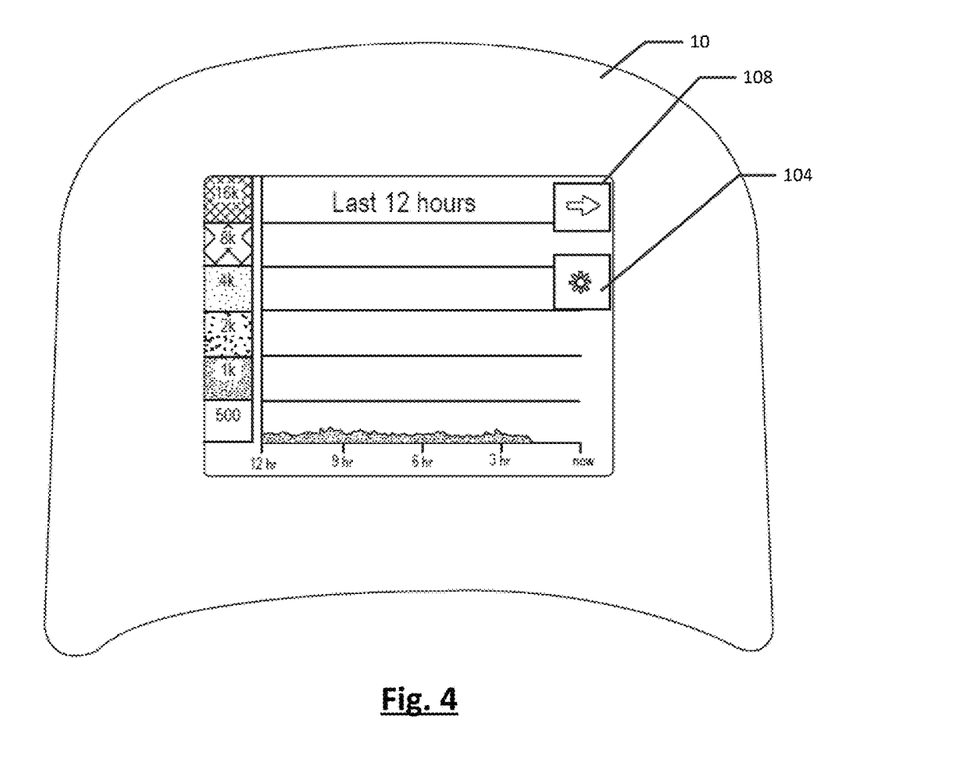
FIGS. 4 and 5 are interactive images of historical air pollution estimates shown on-screen over various time periods in one instantiation of the invention.
Figure 5:
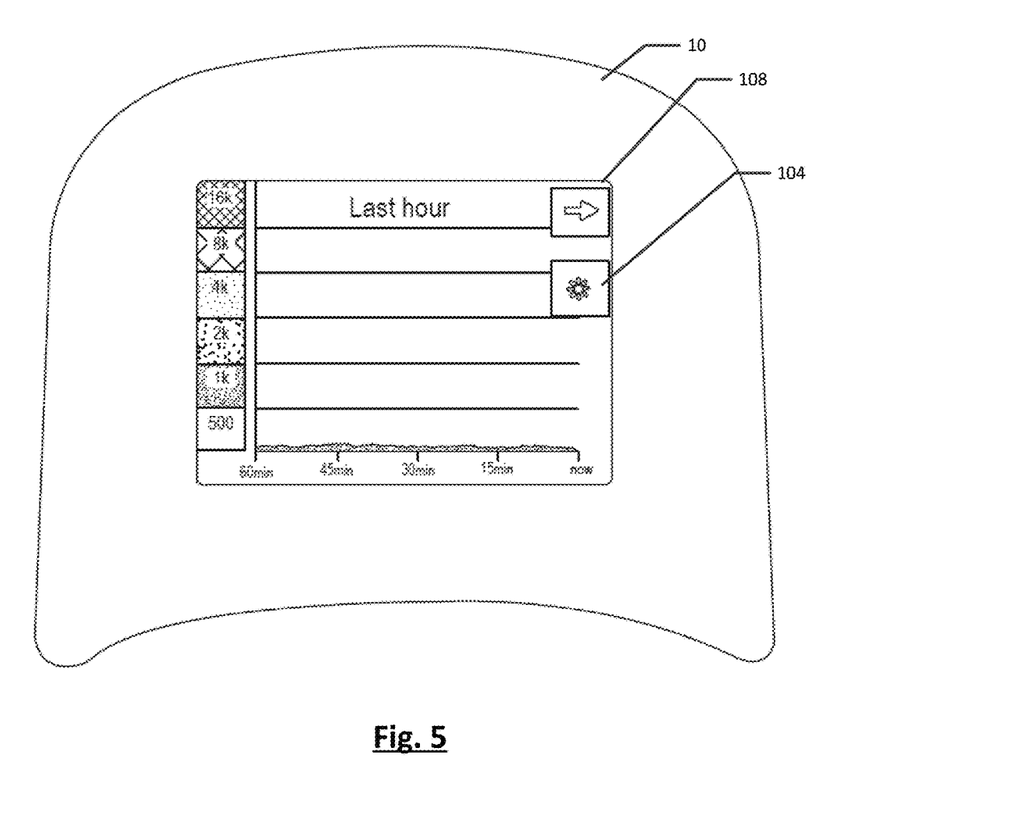

Icons 102 and 104 at the top right in FIG. 3 represent user touch points for transitions to additional interface screen modes. For example, by touching or otherwise activating icon 102, the user can cause the screen to display historical air quality measures over various time spans. Examples of such screens are shown in FIGS. 4 and 5, described below. Activating icon 104 allows the user to adjust settings for the sensor (screen brightness, display and audio settings, Wi-Fi settings, input a geographic location, etc.). Finally, the icon 106 at the lower right can provide status information regarding Wi-Fi connectivity (in the illustrated example, the icon 106 indicates that there is Wi-Fi connectivity; the same symbol with a line through it can indicate no Wi-Fi connectivity, for example). The screen 18 may also display alert message notifications when appropriate.

FIGS. 4 and 5 depict examples of historical interactive screen modes over different time horizons. FIG. 4 shows an example 12-hour view and FIG. 5 shows an example one-hour view. In various embodiments, the user could tap icon 102 in FIG. 3 once for the 12-hour view to be displayed, and tap it twice for the one-hour view to be displayed. In the illustrated examples, the historical views show a two-dimensional graph of the determined air quality values over time, calibrated to X-axis (time) and Y-axis (magnitude of air quality measure, in this case, particles per liter) legends. The color coding in the graph background preferably corresponds to the same color background bins presented on the real-time air quality interactive screen (FIG. 3), reinforcing the overall quality of the air while providing trending information regarding recent changes in air quality. The user could toggle between particles per liter and particle weight by tapping the graph, for example. The user could also return to the real-time mode screen (e.g., FIG. 3) by tapping the return icon 108 in the upper right.

The wireless transceiver subsystem 20 is commanded by the microprocessor 14 to establish, in various embodiments, a Wi-Fi connection to pre-configured Wi-Fi stations; establish an authenticated connection to Internet-based storage servers; and transmit air quality estimates and raw values from sensor 10 continuously. Preferable, the memory 16 significantly exceeds storage requirements for one month of continuous air quality data, thus serving as a local buffer to ensure that no data is lost even in applications where Wi-Fi connectivity may be lost or unavailable for transient periods of time. Depending on specific application requirements, installed collections of the present invention may be produced without a touch-screen display, if for instance all data is to be monitored remotely at all times. Similarly air quality systems without Wi-Fi capability can be implemented with on-board memory sufficient for several years of data storage for applications where Wi-Fi cannot be available.

The particle sensor 12 can be a low-cost scattered-light measuring device with insufficient manufacturing consistency for generalized calibration. In such cases, each air quality sensor 10 should be calibrated to compensate for response variation between individual particle sensors, in order to minimize error between each air quality sensor and professional-grade, calibrated, laser-based particle-counting devices. This calibration process can consist of error minimization by directly adjusting the values of all numerical constants in the estimation algorithm for each sensor 10. This process can be effected, in various embodiments, by placing one or more assembled air quality sensors in a test chamber together with one or more high-performance, typically laser-based (as opposed to LED), calibrated particle-counting devices (e.g., the "reference" device(s)). In various embodiments, the reference device may be a HHPC-6 and/or HHPC-6+ particle counter. In various embodiments, the calibration process involves co-locating all of the air quality sensors and the reference particle-counting device, and connecting them to a transient local Wi-Fi network. In cases where the calibrated, reference particle-counters do not have Wi-Fi capability, their digital access ports can be used to directly connect calibrated outputs to a custom microprocessor package that provides this specific Wi-Fi capability. During calibration a local server receives signals from all connected devices, computes least-squared-error parameter values for all numerical constants in the estimation algorithm (e.g., A, B and D in Equation 1 above), performs error bounds checking, and finally transmits individualized calibration values to all air quality sensors. Each air quality sensor, in turn, stores its final calibration parameters in memory 16 and utilizes the stored parameters for all air quality estimates thereafter.

Referring back to FIG. 1, the sensor 10 may be in wireless communication (via the wireless transceiver circuit 20) with a remote web server 30 via an electronic data communication network 32, such as the Internet. During configuration by its user, each air quality sensor can be registered with the remote web server 30 using its unique microprocessor serial number, and the server 30 establishes an authenticated data feed service for the air quality sensor 10 associated with the credentials of the user. During real-time use, the air quality sensor 10 can establish an authenticated connection to the web server 30, and then presents each channel of environmental data, tagged with a timestamp provided by the sensor's real-time clock, to the server 30 at an adjustable reporting rate. In this embodiment, the sensor 10 reports both raw particle sensor outputs and estimated air quality values to the server 30 in increments adjustable from five seconds to five minutes. The web server 30, in turn, receives authenticated sensor feed data, stores each channel of data together with its timestamp, and provides multiresolution data feeds for each such air quality sensor to authenticated visualization tools, as may be extant on the user's computer device 34. When the web server 30 has successfully received and stored each data packet, it can report successful completion to the air quality sensor 10, which in turn chooses to delete the data locally in order to provide ongoing memory for future air quality estimates.

A remote user, at a client user computer device 34, that is associated with a particular air quality sensor 10 could log into a web site hosted by the web server 30 to view and download air quality readings from the web site. Once the user is viewing the air quality estimates, the user can adjust the temporal resolution to see, at the macro level, trends in air quality values over the course of weeks and months. This enables viewing of general air quality dynamics before and after a HEPA filter in the forced-air system of a home has been replaced, to see if the HEPA filter significantly improves air quality when the HVAC system engages. Furthermore, temporal comparison of air quality values immediately following HEPA filter replacement with current air quality values enables the homeowner to ascertain the ongoing efficacy of the filter, and whether it is time to replace the filter once again. The user can also choose any temporal resolution and temporal horizon, then request immediate export of the data to a comma delimited data file, enabling storage on a local computer. The system thereby affords the user the ability to open their own air quality data in numerical applications such as Microsoft Excel and generate custom views and analyses. This analysis, in turn, can be shared with experts and colleagues to aid with joint problem-solving activities regarding home air pollution issues.

Referring back to FIGS. 3-5, in various embodiments, the sensor 10 can also display outdoor air quality in the bottom right corner by accessing real-time data from a geographically-close outdoor air quality monitor 40, which can report its captured data in real-time to an air quality web server system 42 that the sensor 10 can connect to via the network 32. Or the sensor 10 can connect directly to the outdoor air quality monitor 40 via the network 32. The identity of the appropriate monitor 40 can be ascertained using a spatial search based on the registered position of the air quality sensor (e.g., zip code), as specified by the user.

The network 32 may be a computer data network comprising, for example, an interconnection of a number of data networks (that employ, for example, TCP/IP protocol), such as LANs, WANs, corporate area networks (CAN), an Internet area network (IAN or cloud), or the internet, for example. The client user computer device 34 may be any computer device with a processor that can connect to the network 32, such as personal computer, laptop, smartphone, server, etc.

The sensor unit 10 can be powered by a USB cable, an internal power supply (e.g., batteries), and/or an AC power cord in various embodiments.

In one general aspect, therefor, the present invention is directed to an air quality sensor that comprises an optical particle sensor 12 and a programmable processor circuit 14 that is in communication with the optical particle sensor 10. The optical particle sensor 12 detects particles having a size of 10 microns or less in diameter (e.g., $PM_{2.5}$ particles) in ambient air of the optical particle sensor 12. The programmable processor circuit 14 is programmed to continuously compute updated air quality measures for the ambient air using an estimation algorithm based on pulses in an output signal from the particle sensor over time. In various implementations, the air quality measure can be a cumulative particle density value and/or a cumulative particle weight value. Also, the optical particle sensor 12 may comprise a LED and accordingly detect particles based on reflection of light energy from the LED by particles in a chamber of the sensor.

In various implementations, the output signal of the particle sensor 12 has a duty cycle that is approximately proportional to the number of particles detected by the sensor. In such cases, the programmable processor circuit may compute the updated cumulative air quality measure by performing operations that comprise: (i) adjusting a current value of the cumulative air quality measure at a first rate proportional to a difference between the current value and a raw value from the sensor, scaled by a constant, when the raw value is non-zero; and (ii) exponentially decaying the current value of the cumulative air quality measure toward zero at a second rate when the raw value is zero, where the second rate is less than the first rate. Also, the estimation algorithm may comprise a combination of linear proportional transfer functions from sensor events (e.g., pulses) to calibrated air quality values. Parameters of the estimation algorithm may be calibrated by minimizing errors relative to a reference particle detector, which may be a laser-based reference particle detector.

The air quality sensor may further comprise a display 18 in communication with the processor circuit that displays real-time and historical air quality measures computed by the processor circuit. The displays may be separate view. For example, FIG. 3 shows a current value, whereas FIGS. 4 and 5 show historical values. The display may be a touch screen display for receiving the user display selection inputs (e.g., real-time versus historical view). The historical view may be a graph of the air quality measure over a time period of one or more hours. The air quality sensor may additionally comprise a wireless transceiver circuit in communication with the processor circuit, for wirelessly transmitting the air quality measures computed by the processor circuit to a remote server via an electronic data communication network.

In another general aspect, the present invention is directed to an air quality sensor that comprises: (i) an optical particle sensor for detecting particles having a size of 10 microns or less in diameter in ambient air of the optical particle sensor; (ii) a programmable processor circuit in communication with the optical particle sensor for computing a continuously updated cumulative air quality measure for the ambient air based on an output signal from the optical particle sensor; (iii) a memory unit for storing the continuously updated cumulative air quality measures computed by the processor circuit; and (iv) a display in communication with the processor circuit that displays real-time and historical air quality measures computed by the processor circuit and stored in the memory unit.

A method according to one general aspect of the present invention may comprise the steps of: (i) detecting particles having a size of 10 microns or less in diameter in ambient air with an optical particle sensor, where the optical particle sensor comprises a LED and detects particles based on reflection of light energy from the LED by particles in a chamber of the sensor; and (ii) computing, by a programmable processor circuit that is in communication with the optical particle sensor, a continuously updated cumulative air quality measure for the ambient air using an estimation algorithm based on pulses in the output signal from the sensor over time. The method may additionally comprise the step of wirelessly transmitting, by a wireless transceiver circuit that is in communication with the processor circuit, the air quality measures computed by the processor circuit to a remote server via an electronic data communication network.

In various embodiments disclosed herein, a single component may be replaced by multiple components and multiple components may be replaced by a single component to perform a given function or functions. Except where such substitution would not be operative, such substitution is within the intended scope of the embodiments. Any servers described herein, for example, may be replaced by a "server farm" or other grouping of networked servers (such as server blades) that are located and configured for cooperative functions. It can be appreciated that a server farm may serve to distribute workload between/among individual components of the farm and may expedite computing processes by harnessing the collective and cooperative power of multiple servers. Such server farms may employ load-balancing software that accomplishes tasks such as, for example, tracking demand for processing power from different machines, prioritizing and scheduling tasks based on network demand and/or providing backup contingency in the event of component failure or reduction in operability.

While various embodiments have been described herein, it should be apparent that various modifications, alterations, and adaptations to those embodiments may occur to persons skilled in the art with attainment of at least some of the advantages. The disclosed embodiments are therefore intended to include all such modifications, alterations, and adaptations without departing from the scope of the embodiments as set forth herein.

What is claimed is:

1. An air quality sensor comprising:
an optical particle sensor for detecting particles having a size of 10 microns or less in diameter in ambient air of the optical particle sensor, wherein the optical particle sensor outputs an output signal;
wherein the optical particle sensor comprises a LED and detects particles based on reflection of light energy from the LED by particles in a chamber of the optical particle sensor; and
a programmable processor circuit in communication with the optical particle sensor that is programmed to continuously compute updated air quality measures for the ambient air using an estimation algorithm based on pulses in the output signal from the optical particle sensor over time;
wherein the programmable processor circuit computes the updated air quality measures by performing operations that comprise:
adjusting a current value of the air quality measure at a first rate proportional to a difference between the current value and a raw value from the optical particle sensor, scaled by a constant, when the raw value is non-zero; and exponentially decaying the current value of the air quality measure toward zero at a second rate when the raw value is zero, wherein the second rate is less than the first rate.

2. The air quality sensor of claim 1, wherein the air quality measure comprises a particle density value.

3. The air quality sensor of claim 1, wherein the air quality measure comprises a particle weight value.

4. The air quality sensor of claim 1, wherein the output signal of the optical particle sensor has a duty cycle that is approximately proportional to the number of particles detected by the optical particle sensor.

5. The air quality sensor of claim 1, wherein the estimation algorithm comprises a combination of linear proportional transfer functions from sensor events to calibrated air quality values.

6. The air quality sensor of claim 5, wherein parameters of the estimation algorithm are calibrated by minimizing error relative to a reference particle detector.

7. The air quality sensor of claim 6, wherein the reference particle detector comprises a laser-based reference particle detector.

8. The air quality sensor of claim 1, further comprising a display in communication with the processor circuit that displays real-time and historical air quality measures computed by the processor circuit.

9. The air quality sensor of claim 8, wherein the display displays the real-time and historical air quality measures in separate views upon receiving a user display selection input.

10. The air quality sensor of claim 9, wherein the display comprises a touch screen display for receiving the user display selection inputs.

11. The air quality sensor of claim 9, wherein the display of the historical air quality measures comprises a graph of the air quality measure over a time period of one or more hours.

12. The air quality sensor of claim 1, further comprising a wireless transceiver circuit in communication with the processor circuit, wherein the wireless transceiver circuit is for wirelessly transmitting the air quality measures computed by the processor circuit to a remote server via an electronic data communication network.

13. A method of determining the quality of ambient air, comprising:
  detecting particles having a size of 10 microns or less in diameter in ambient air with an optical particle sensor, wherein the optical particle sensor comprises a LED and detects particles based on reflection of light energy from the LED by particles in a chamber of the optical particle sensor, and wherein the optical particle sensor outputs an output signal; and
  computing, by a programmable processor circuit that is in communication with the optical particle sensor, a continuously updated air quality measure for the ambient air using an estimation algorithm based on pulses in the output signal from the optical particle sensor over time;
  wherein computing the continuously updated air quality measure comprises:
    adjusting a current value of the air quality measure at a first rate proportional to a difference between the current value and a raw value from the optical particle sensor, scaled by a constant, when the raw value is non-zero; and
    exponentially decaying the current value toward zero at a second rate when the raw value is zero, wherein the second rate is less than the first rate.

14. The method of claim 13, wherein the output signal of the optical particle sensor has a duty cycle that is approximately proportional to a number of particles detected by the optical particle sensor.

15. The method of claim 13, further comprising, prior to computing the air quality measures, calibrating parameters of the estimation algorithm by minimizing errors relative to a reference particle detector.

16. The method of claim 13, further comprising displaying, by a display that is in communication with the processor circuit, real-time and historical air quality measures computed by the processor circuit.

17. The method of claim 13, further comprising, wirelessly transmitting the computed air quality measures, by a wireless transceiver circuit that is in communication with the processor circuit, to a remote server via an electronic data communication network.

18. An air quality sensor comprising:
  an optical particle sensor for detecting particles having a size of 10 microns or less in diameter in ambient air of the optical particle sensor;
  wherein the optical particle sensor comprises a LED and detects particles based on reflection of light enemy from the LED by particles in a chamber of the optical particle sensor;
  a programmable processor circuit in communication with the optical particle sensor for computing a continuously updated air quality measure for the ambient air based on an output signal from the optical particle sensor;
  wherein the programmable processor circuit computes the continuously updated air quality measure by performing operations that comprise:
    adjusting a current value of the air quality measure at a first rate proportional to a difference between the current value and a raw value from the optical particle sensor, scaled by a constant, when the raw value is non-zero; and
    exponentially decaying the current value of the air quality measure toward zero at a second rate when the raw value is zero, wherein the second rate is less than the first rate;
  a memory unit for storing the continuously updated air quality measures computed by the processor circuit; and
  a display in communication with the processor circuit that displays real-time and historical air quality measures computed by the processor circuit and stored in the memory unit.

19. The air quality sensor of claim 18, wherein the display displays the real-time and historical air quality measures in separate views upon receiving a user display selection input.

20. The air quality sensor of claim 19, wherein the display comprises a touch screen display for receiving the user display selection inputs.

21. The air quality sensor of claim 19, further comprising a wireless transceiver circuit in communication with the processor circuit, wherein the wireless transceiver circuit is for wirelessly transmitting the air quality measures computed by the processor circuit to a remote server via an electronic data communication network.

22. A method of determining the quality of ambient air comprising:
  detecting particles having a size of 10 microns or less in diameter in ambient air with an optical particle sensor, wherein the optical particle sensor comprises a LED and detects particles based on reflection of light energy from the LED by particles in a chamber of the optical, particle sensor;

computing, by a programmable processor circuit that is in communication with the optical particle sensor, continuously updated air quality measures for the ambient air based on an output signal from the optical particle sensor;

wherein computing the continuously updated air quality measures comprises:
- adjusting a current value of the air quality measure at a first rate proportional to a difference between the current value and a raw value from the optical particle sensor, scaled by a constant, when the raw value is non-zero; and
- exponentially decaying the current value toward zero at a second rate when the raw value is zero, wherein the second rate is less than the first rate;

storing, in a memory unit associated with the processor circuit, the continuously updated air quality measures computed by the processor circuit; and visually displaying, on a display in communication with the processor circuit, real-time and historical air quality measures computed by the processor circuit and stored in the memory unit.

23. The method of claim 22, wherein displaying the real-time and historical air quality measures comprises displaying the real-time and historical air quality measures in separate views upon receiving a user display selection input.

24. The method of claim 23, wherein the display comprises a touchscreen interface, and where the method further comprises receiving the user display selection inputs via the touchscreen interface.

25. The method of claim 23, further comprising wireless transmitting, by a wireless transceiver circuit that is in communication with the processor circuit, the air quality measures computed by the processor circuit to a remote server via an electronic data communication network.

* * * * *